United States Patent [19]

Steltenkamp et al.

[11] Patent Number: 5,573,700
[45] Date of Patent: Nov. 12, 1996

[54] LIQUID HOUSEHOLD CLEANING COMPOSITION WITH INSECT REPELLENT

[75] Inventors: Robert J. Steltenkamp, Somerset; John H. Puckhaber, Jr., Flemington; Daniel Colodney, Hampton; Thomas C. Hendrickson, South River, all of N.J.

[73] Assignee: Colgate-Palmolive Co., New York, N.Y.

[21] Appl. No.: 440,598

[22] Filed: May 15, 1995

Related U.S. Application Data

[63] Continuation of Ser. No. 290,446, Aug. 15, 1994, which is a continuation of Ser. No. 44,138, Apr. 8, 1993, which is a continuation-in-part of Ser. No. 755,276, Sep. 5, 1991, abandoned, which is a continuation-in-part of Ser. No. 734,830, Jul. 24, 1991, abandoned, which is a continuation-in-part of Ser. No. 685,329, Apr. 15, 1991, Pat. No. 5,258,408, which is a continuation of Ser. No. 612,747, Nov. 13, 1990, Pat. No. 5,182,304, which is a continuation of Ser. No. 267,141, Nov. 4, 1988, Pat. No. 5,006,562, which is a continuation-in-part of Ser. No. 894,985, Aug. 8, 1986, abandoned, which is a continuation-in-part of Ser. No. 71,305, Jul. 16, 1987, Pat. No. 4,804,683.

[51] Int. Cl.⁶ .............................. A01N 25/00; C11D 1/00
[52] U.S. Cl. .................. 510/383; 424/405; 424/DIG. 10; 510/192; 510/218
[58] Field of Search ........................... 252/106, 544, 252/DIG. 14, 173; 424/405, DIG. 10; 514/613, 617, 625, 629, 919; 564/215

[56] References Cited

U.S. PATENT DOCUMENTS

| | | | |
|---|---|---|---|
| 3,738,943 | 6/1973 | Kaneko | 252/540 |
| 4,443,363 | 4/1984 | Klinger et al. | 252/547 |
| 4,455,308 | 6/1984 | Smolanoff | 424/248.57 |
| 4,612,327 | 9/1986 | Matukuma et al. | 514/479 |
| 4,668,434 | 5/1987 | Bowman | 252/522 A |
| 4,707,496 | 11/1987 | Simmons | 514/531 |
| 4,804,683 | 2/1989 | Steltenkamp | 514/629 |
| 4,983,391 | 1/1991 | Muneyuki et al. | 424/408 |
| 5,006,562 | 4/1991 | Steltenkamp | 514/625 |
| 5,109,022 | 4/1992 | Jeanne et al. | 514/552 |
| 5,182,304 | 1/1993 | Steltenkamp | 514/625 |
| 5,258,408 | 11/1993 | Steltenkamp | 514/625 |
| 5,292,504 | 3/1994 | Cardin et al. | 424/70 |
| 5,298,250 | 3/1994 | Lett et al. | 424/405 |
| 5,298,528 | 3/1994 | Evers | 514/626 |

FOREIGN PATENT DOCUMENTS

| | | |
|---|---|---|
| 0090288 | 10/1983 | European Pat. Off. . |
| 0149051 | 7/1985 | European Pat. Off. . |
| 0367257 | 5/1990 | European Pat. Off. . |
| 2602506 | 2/1988 | France . |

OTHER PUBLICATIONS

Charles R. Worthing et al. "The Pesticide Manual" (9th Edition) 1991 The British Crop Protection Council Farnham, Surrey GB (no month).

*Primary Examiner*—Gary P. Straub
*Assistant Examiner*—Timothy C. Vanoy
*Attorney, Agent, or Firm*—Bernard Lieberman; James M. Serafino

[57] ABSTRACT

An aqueous liquid detergent composition is provided for cleaning a hard surface and for repelling insects therefrom comprising a detersive proportion of a surface active detergent compound, an effective amount of an insect repellent material which is sufficient to repel insect from the hard surface after application of the detergent composition thereto, the liquid detergent composition being substantially free of a liquid hydrocarbon.

9 Claims, 1 Drawing Sheet

LIQUID HOUSEHOLD CLEANING COMPOSITION WITH INSECT REPELLENT

BACKGROUND OF THE INVENTION

This is a Continuation of application Ser. No. 08/290,446, filed Aug. 15, 1994, now abandoned which is a continuation of Ser. No. 08/044,138, filed Apr. 8, 1993, now abandoned, which is a continuation-in-part of co-pending U.S. application Ser. No. 07/755,276 filed Sep. 5, 1991, now abandoned which is a continuation-in-part of U.S. Ser. No. 07/734,830, filed Jul. 24, 1991, now abandoned which is a continuation-in-part of U.S. Ser. No. 07/685,329, filed Apr. 15, 1991, now U.S. Pat. No 5,258,408, which is a continuation of U.S. Ser. No. 07/612,747 filed, Nov. 13, 1990, now U.S. Pat. No. 5,182,304, which is a continuation of U.S. Serial No. 07/267,141, filed Nov. 4, 1988, now U.S. Pat. No. 5,006,562, which is a continuation-in-part of U.S. patent applications Ser. No. 06/894,985, filed Aug. 8, 1986, now abandoned and Ser. No. 07/071,305, filed Jul. 16, 1987, now U.S. Pat. No. 4,804,683, the disclosures of which are incorporated herein by reference.

This invention relates to liquid detergent compositions suitable for cleaning hard surfaces and which impart insect repelling properties. More particularly, this invention relates to liquid all purpose detergent compositions containing an insect repellent material, and to a process for cleaning and repelling insects from surfaces and articles to which such detergent compositions are applied.

Many types of insects common in households, such as German (Blattela germanica) or house cockroaches, are classified as pests, and much effort has been made to eradicate or at least to control them. Mosquito repellents have long been marketed and various chemicals that are effective in repelling roaches have been discovered. Typically, these chemicals and repellents are used in the household by applying or spraying them to surfaces of walls, floors, cabinets, drawers, packages, containers, rugs, upholstery and carpeting, and in potential nesting places for insects, such as inside walls and between floors. However, heretofore insect repellents have not been generally used in conjunction with hard surface cleaners so as to effectively clean a hard household surface, such as a kitchen wall, oven top, bathroom floor or the like, while at the same time applying a film of insect repellent material which is sufficiently substantive to the surface to which the composition is applied to repel insects therefrom.

The incorporation of an insect repellent into a polishing product for household floors is known in the art. U.S. Pat. No. 3,018,217 to Bruce discloses floor wax coating compositions containing dibutyl succinate as an insect repellent. U.S. Pat. No. 3,034,950 to Goodhue et al, discloses a class of insect repellent compounds which may be applied to surfaces dispersed in a wax. In U.S. Pat. No. 4,455,308 to Smolanoff, there are described insect repellent formulations containing a liquid carrier such as liquid aliphatic or aromatic hydrocarbons. An emulsifying agent such as a nonionic surfactant may be added to the liquid hydrocarbon to permit the composition to be dispersed in water for end use application. U.S. Pat. No. 4,822,614 to Rodero, discloses an insect-repellent ingredient in a hydrocarbon-based solvent such as isoparaffinic hydrocarbons.

SUMMARY OF THE INVENTION

The present invention provides an aqueous liquid detergent composition capable of cleaning a hard surface and repelling insects therefrom comprising (i) a detersive proportion of a surface active detergent compound selected from the group consisting of anionic, nonionic, cationic and amphoteric detergent compounds; (ii) at least about 50%, by weight, water; and (iii) an effective amount of an insect repellent material which is sufficient to repel insects from such hard surface after application of the detergent composition thereto. The liquid detergent composition is free of an insecticide.

The present invention is predicated on the discovery that the insect repellent properties of a repellent material is enhanced with regard to a specific area or location when such area or location is cleaned with a detergent composition as herein described. This effect may be attributed to the natural tendency of insects to preferentially congregate in soiled areas rather than upon a cleaned surface as well as the increased substantivity of the insect repellent material to such washed or cleaned surfaces.

The term "insect" is used herein in its broad sense and, is intended to encompass cockroaches, such as the German (Blattela germanica) and American (Periplaneta americana) roach, as well as mosquitoes, moths, flies, fleas, ants, lice and arachnids, such as spiders, ticks and mites.

The term "insect repellent material" is intended to encompass a wide variety of materials having insect repellent properties which are compatible with the type of detergent composition described herein and which manifest a sufficient substantivity to the hard surface to which the detergent composition is applied to be efficacious as a repellent.

Included among the insect repellent materials useful for the present invention are the following compounds which may be used individually or in combination with other repellent materials, the designation in parenthesis following certain compound names referring to its commercial or common designation:

N-alkyl neoalkanamides wherein the alkyl is of 1 to 4 carbon atoms, and the neoalkanoyl moiety is of 7 to 14 carbon atoms:

N,N-diethyl-meta-toluamide (DEET);

2-Hydroxyethyl-n-octyl sulfide (MGK 874);[1]

[1] MGK Repellents are trademarks of McLaughlin Gormley King Company; Minneapolis; Minn., USA.

N-Octyl bicycloheptene dicarboximide (MGK 264);

A preferred mixture of the above two materials comprising 66% MGK 264 and 33% MGK 874;

Hexahydrodibenzofuran carboxaldehyde (MGK 11);

Di-n-propyl isocinchomerate (MGK 326);

2-Ethyl-1,3-hexanediol (Rutgers 612);

2-(n-butyl)-2-ethyl-1,3-propanediol;

Dimethyl phthalate;

Dibutyl succinate (Tabutrex);

Piperonyl butoxide; and

Pyrethrum

Although the above-mentioned insect repellent materials are longer lasting and are preferred for purposes of the present invention, other useful repellent materials include essential oils such as Mentha arvensis (Cornmint); Mentha piperita (Peppermint); Mentha spicata (American Spearmint); Mentha cardica (Scotch Spearmint); Lemongrass East Indian Oil; Lemon Oil; Citronella; Cedarwood (Juniperus virginiana L.); and Pine Oil. Terpenoids are another class of materialshaving insect repellent properties, the most useful being (−)-Limonene; (+)-Limonene; (−)-Carvone; Cineole (Eucalyptol); Linalool; Gum Camphor; Citronellal; Alpha and Beta -Terpineol; Fencholic acid; Borneol, iso Borneol, Bornyl acetate and iso Bornyl acetate.

Among the non-commercial repellent materials useful for the invention are the following:

N,N-Diethyl cyclohexylacetamide (DECA)

1,2,3,6-Tetrahydro-1-(2-methyl-1-oxopentyl) piperidine

N,N-Diethyl-3-cyclohexyl propionamide (DCP)

2-Ethyl-1-(2-methyl-1-oxo-2-butenyl) piperidine

N,N-diethyl nonanamide, and

N,N-Diethyl Phenylacetamide.

With regard to the aforementioned N-alkyl neoalkanamides, the alkyl group is preferably methyl or ethyl, and most preferably is methyl. The neoalkanoyl moiety is preferably neodecanoyl or neotridecanoyl.

DETAILED DESCRIPTION OF THE INVENTION

Figure 1:
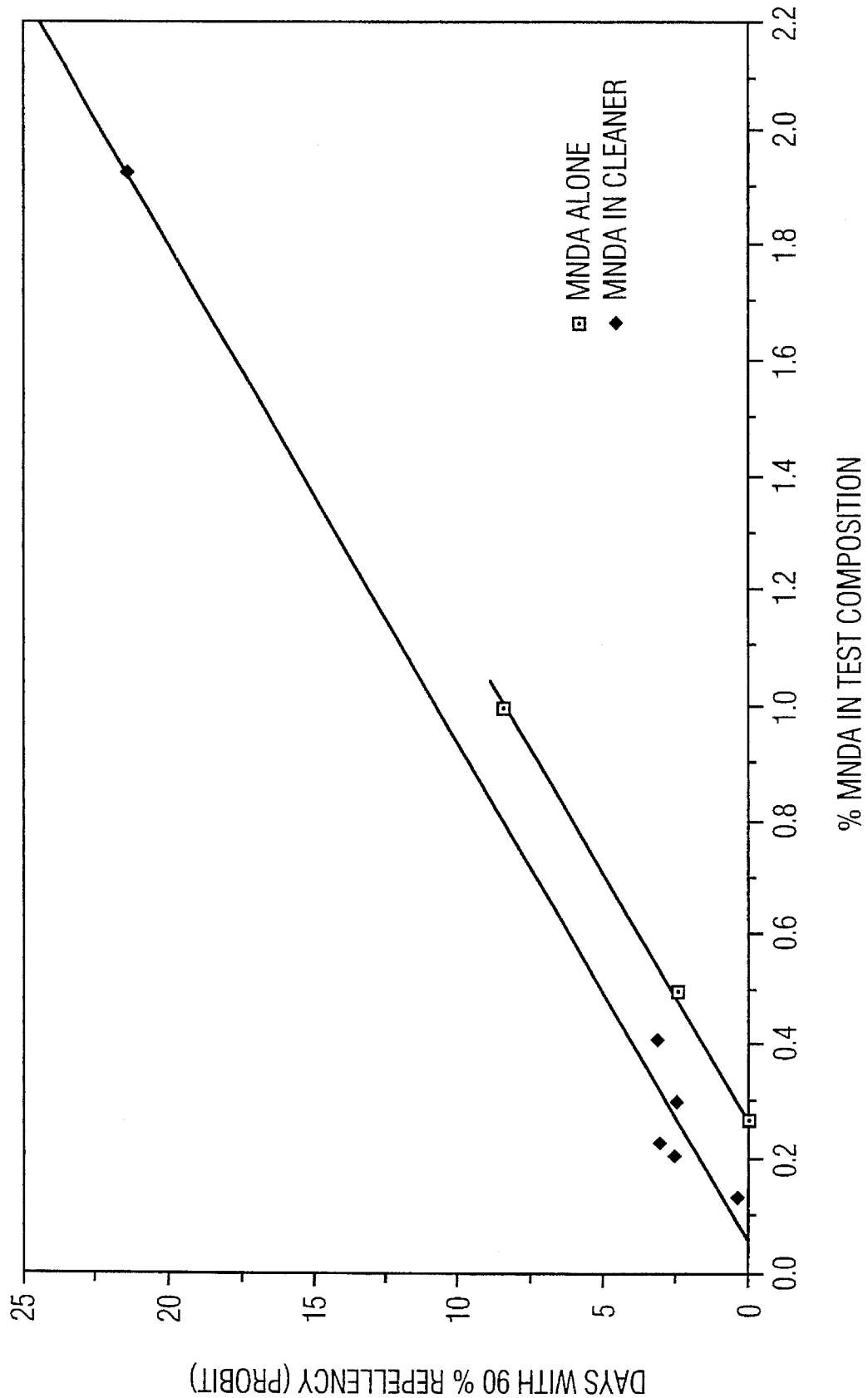
FIG. 1 is a graph showing the number of days with 90% repellency as a function of the percent of MNDA in the test composition.

The detergent compositions of the invention contain a detersive proportion of one or more surface active detergent compounds from among anionic, nonionic, cationic and amphoteric detergents, which generally will be in the range of from about 1 to about 30%, by weight, of the composition, preferably from about 2 to about 20%, by weight. The detergent is preferably a synthetic organic detergent of the anionic or nonionic type and often a combination of anionic and nonionic detergents will be most preferred. Descriptions of many such detergents are found in the text *Surface Active Agents and Detergents,* Vol, II, pages 25–138, by Schwartz, Perry and Berch, published in 1958 by Interscience Publishers, Inc. Such compounds are also described in a 1973 publication by John W. McCutcheon, entitled *Detergents and Emulsifiers.* Both such publications are incorporated herein by reference.

The anionic detergents employed will normally be salts of alkali metals, such as sodium or potassium or ammonium or lower alkanolammonium salts, e.g., triethanolamine salts. The anionic detergent may be a sulfate, sulfonate, phosphate or phosphonate or salt of other suitable acid but usually will be a sulfate or sulfonate. The anionic detergents include a lipophilic group, which will normally have from 10 to 18 carbon atoms, preferably in linear higher alkyl arrangement, but other lipophilic groups may be present instead, preferably including 12 to 16 carbon atoms, such as branched chain alkyl benzene. Examples of suitable anionic detergents include higher fatty alcohol sulfonates, such as sodium tridecyl sulfonate; sodium linear alkyl benzene sulfonates, e.g., sodium linear dodecyldecylbenzene sulfonate; olefin sulfonates; and paraffin sulfonates. The anionic detergents are preferably sodium salts but potassium, ammonium and triethanolammonium salts are often more desirable for some liquid compositions.

The suitable nonionic detergents will normally be condensation products of lipophilic compounds or moieties and lower alkylene oxides or polyalkoxy moieties. Highly preferable lipophiles are higher fatty alcohols of 10 to 18 carbon atoms but alkyl phenols, such as octyl and nonyl phenols, may also be used. The alkylene oxide of preference is ethylene oxide and normally from 3 to 30 moles of ethylene oxide will be present per mole of lipophile. Preferably such ethoxylate content will be 3 to 10 moles per mole of higher fatty alcohol and more preferably it will be 6 to 7 moles, e.g., 6.5 or 7 moles per mole of higher fatty alcohol (and per mole of nonionic detergent). Both broad ranges ethoxylates and narrow range ethoxylate (BRE's and NRE's) may be employed, with the difference between them being in the "spread" of number of ethoxylate groups present, which average within the ranges given. For example, NRE's which average 5 to 10 EtO groups per mole in the nonionic detergent will have at least 70% of the EtO content in polyethoxy groups of 4 to 12 moles of EtO and will preferably have over 85% of the EtO content in such range. BRE nonionic detergents have a broader range of ethoxy contents than NRE's, often with a spread from 1 to 15 moles of EtO when the EtO chain is in the 5 to 10 EtO range (average). Examples of the BRE nonionic detergents include those sold by Shell Chemical Company under the trademark Neodol®, including Neodol 25-7, Neodol 23-6.5 and Neodol 25-3. Supplies of NRE nonionic detergents have been obtained from Shell Development Company, which identifies such materials as 23-7P and 23-7Z.

Cationic surface active compounds may also be employed. They comprise surface active detergent compounds which contain an organic hydrophobic group which forms part of a cation when the compound is dissolved in water, and an anionic group. Typical cationic detergents are amine and quaternary ammonium compounds.

The quaternary ammonium compounds useful herein are known materials and are of the high-softening type. Included are the $N_1N$-di(higher) $C_{14}$–$C_{24}$, $N_1N$-di(lower) $C_1$–$C_4$ alkyl quaternary ammonium salts with water solubilizing anions such as halide, e.g. chloride, bromide and iodide; sulfate, methosulfate and the like and the heterocyclic amides such as imidazolinium.

For convenience, the aliphatic quaternary ammonium salts may be structurally defined as follows:

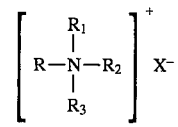

wherein R and $R_1$ represent alkyl of 14 to 24 and preferably 14 to 22 carbon atoms; $R_2$ and $R_3$ represent lower alkyl of 1 to 4 and preferably 1 to 3 carbon atoms, X represents an anion capable of imparting water solubility or dispersibility including the aforementioned chloride, bromide, iodide, sulfate and methosulfate. Particularly preferred species of aliphatic quats include:

distearyl dimethylammonium chloride di-hydrogenated tallow dimethyl ammonium chloride di tallow dimethyl ammonium chloride distearyl dimethyl ammonium methyl sulfate di-hydrogenated tallow dimethyl ammonium methyl sulfate.

Amphoteric detergents are also suitable for the invention. This class of detergents is well known in the art and many operable detergents are disclosed by Schwartz, Perry and Berch in "Surface Active Agents and Detergents", Vol. II, Interscience Publishers, Inc., New York (1958)in Chapter 4 thereof. Examples of suitable amphoteric detergents include: alkyl betaiminodipropionates, $RN(C_2H_4COOM)_2$; and alkyl beta-amino propionates, $RN(H)C_2H_4COOM$.

Builders may be present in the liquid detergent composition in an amount of from about 1 to 20% to improve the detergency of the synthetic organic detergents. Such builders may be inorganic or organic, water soluble or water insoluble. Included among such builders are polyphosphates, e.g., sodium tripolyphosphate; carbonates, e.g., sodium carbonate; bicarbonates, e.g., sodium bicarbonate; borates, e.g., borax; and silicates, e.g., sodium silicate; water insoluble inorganic builders, including zeolites, e.g., hydrated Zeolite 4A; and water soluble organic builders, including citrates, gluconates, NTA, and polyacetal carboxylates.

Various adjuvants may be present in the detergent compositions such as fluorescent brighteners, antistatic agents, antibacterial agents, fungicides, foaming agents, anti-foams, flow promoters, suspending agents, antioxidants, anti-gelling agents, soil release promoting agents, and enzymes.

The liquid detergent compositions of the invention will generally comprise from about 2 to 20% of surface active detergent compounds which are preferably anionic and/or nonionic, from about 1 to 20%, by weight, of builder salts for such detergents and from about 0.2 to 20%, preferably 0.5 to 10%, by weight, of the insect repellent material, the balance being predominantly water, adjuvants and optionally an emulsifying agent, or hydrotrope such as sodium toluene sulfonate or a solvent suitable for the insect repellent material such as isopropyl alcohol or acetone. To facilitate the incorporation of a fragrance or perfume into the aqueous liquid detergent composition, it is often advantageous to formulate the liquid detergent composition in microemulsion form with water as the continuous phase and oil or hydrocarbon as the dispersed phase.

In practical tests, on actual kitchen floors, counters, drainboards and walls, and in kitchen cabinets and under refrigerators, in roach-infested apartments, significantly fewer roaches will be observed on surfaces to which or near which the invented liquid detergent compositions are applied than on control surfaces, and fewer roaches are found on the bottoms and shelves of cabinets and pantries when walls thereof are treated with the invented detergent compositions. When floors, walls, counters, sinks, cabinets and doors in a house or apartment are treated with the liquid detergent compositions of the invention, the incidence of cockroach infestation is reduced, compared to control apartments where no repellent is applied.

EXAMPLE 1

A single composition in accordance with the invention formulated as shown below was used as the starting material to prepare by dilution six liquid compositions of varying degrees of dilution containing six correspondingly different levels of N-methyl neodecanamide (MNDA) insect repellent material.

| LIQUID HARD SURFACE CLEANER | |
|---|---|
| COMPONENT | WEIGHT PERCENTAGE |
| Sodium linear dodecylbenzene sulfonate | 4 |
| Nonionic detergent[1] | 2 |
| MNDA | 2.0 |
| Coconut fatty acid | 0.5 |
| Soda ash | 2 |
| Sodium bicarbonate | 1 |
| Isopropyl alcohol | 4 |
| Water | Balance |
| Fragrance | 1 |

[1]Condensation product of one mole of a mixture of fatty alcohols of 9–11 carbon atoms with 6 moles of ethylene oxide.

The percentage of MNDA in each of the six tested detergent compositions varied, respectively, as follows: 0.12, 0.20, 0.22, 0.29, 0.4 and 2.0%

The insect repellency of each of these six hard surface cleaning detergent compositions was tested by the procedure described below and compared with the repellency imparted by three repellent-containing comparative compositions, i.e. three solutions of acetone containing 0.25, 0.5 and 1.0%, by weight, respectively, of MNDA.

TEST PROCEDURE

Insects—German and American cockroaches were from established colonies maintained at 27° C. Carpenter ant workers were collected from a log containing a queenright colony and were kept in the same conditions as the cockroaches.

Bioassay—Forty-eight hours prior to initiation of an assay, 50 male German cockroaches were allowed to acclimate to the plastic test cages (51×28×20 cm) with food and water available in the center. A thin film of teflon emulsion (Fluon AD-1, Northern products, Woonsocket, R.I.) on the sides of the cages restricted the insects to the floor of the cage. The assays used either 50 female German cockroaches, 20 males American Cockroaches, or 50 carpenter ant workers.

The repellency of the various compositions to be tested were evaluated over time. The procedure consisted of arranging five 3×3 inch asphalt tiles into a cubic shelter ("cup") and treating the tiles with the various test compositions. The treated sides faced inward. The method relies on the light avoidance response of the cockroaches. Two milliliters of a test composition was applied to the entire inside surface of the cup. Control cups were treated with acetone or water only. The cups were allowed to dry for 1 hr and then a control and a treated cup were inverted into each of the test cages. Food and water were provided in the center of each cage, outside of the cups. The number of insects resting on the inner walls of each cup were recorded in the middle of the photophase daily for 25 days or until equal numbers were found in treated and untreated cups. After each count the insects were disturbed and the positions of the treated and control cups were reversed. Accordingly, the distribution of cockroaches for any given day is considered independent of the previous days distribution.

Repellency was defined as the percentage of insects that avoided the treated surfaces and was calculated as $$\% \text{ Repellency} = 100 - \frac{100 \times (N_t)}{(N_t + N_c)}$$

where $N_t$ is the number of insects on the treated surface and $N_c$ is the number on the acetone treated control surfaces. The repellency of compounds was evaluated on the basis of the number of days of 90% repellency which is based on (i) the number of days of complete (100%) repellency and (ii) a maximum likelihood probit analysis of time/repellency (SAS User's Guide, SAS Institute 1985) from which a measure was calculated of the number of days of 90% repellency ($RT_{90-10}$% of the insects on the treated surface, 90% on the control surface).

The results of the repellency tests are indicated in FIG. 1 which is a graph showing the number of days with 90% repellency as a function of the percent of MNDA in the test composition.

As noted in the FIGURE, the comparative compositions not in accordance with the invention were unable to achieve 90% repellency at a level of MNDA repellent of 0.25%. In contrast thereto, the compositions of the invention were able to provide almost 3 days of 90% repellency at a 0.2% level of MNDA.

We claim:

1. An aqueous liquid detergent composition for cleaning a household hard surface and for repelling insects therefrom comprising
   (i) a detersive proportion of a surface active detergent compound selected from the group consisting of anionic, nonionic, cationic and amphoteric detergent compounds and mixtures thereof;
   (ii) at least about 50%, by weight, water; and
   (iii) an effective amount of an insect repellent material which is sufficient to repel insects from such hard surface after application of the liquid detergent composition thereto, said liquid detergent composition being free of an insecticide.

2. A liquid detergent composition as in claim 1 further including a water-soluble solvent for said insect repellent material.

3. A liquid detergent composition as in claim 2 wherein said solvent is isopropyl alcohol.

4. A liquid detergent composition as in claim 1 comprising from about 2 to 20%, by weight, of said surface active detergent compounds, from about 1 to 20%, by weight, of a builder salt, and from about 0.2 to 20%, by weight, of said insect repellent material.

5. A liquid detergent composition as in claim 4 wherein said insect repelling material is $N_1N$-diethyltoluamide.

6. A process for cleaning a household hard surface and for repelling insects therefrom comprising applying to said hard surface a liquid detergent composition comprising
   (i) a detersive proportion of a surface active detergent compound selected from the group consisting of anionic, nonionic, cationic and amphoteric detergent compounds;
   (ii) at least about 50%, by weight, water; and
   (iii) an effective amount of an insect repellent material which is sufficient to repel insects from such hard surface after application of the liquid detergent composition thereto, said liquid detergent composition being free of an insecticide.

7. A process according to claim 6 wherein said detergent composition further includes a solvent for said insect repellent material.

8. A process according to claim 7 wherein said solvent is isopropyl alcohol.

9. A process according to claim 6 wherein said detergent composition comprises from about 2 to 20%, by weight, of said surface active detergent compound, from about 1 to 20%, by weight, of a builder salt, and from about 0.2 to 20%, by weight, of said insect repellent material.

* * * * *